(12) United States Patent
Kim

(10) Patent No.: US 6,780,641 B2
(45) Date of Patent: Aug. 24, 2004

(54) IMMORTALIZED HUMAN MICROGLIA CELL LINE

(75) Inventor: Seung U. Kim, Vancouver (CA)

(73) Assignee: University of British Columbia, Vancover (CA)

( * ) Notice: Subject to any disclaimer, the term of this patent is extended or adjusted under 35 U.S.C. 154(b) by 0 days.

(21) Appl. No.: 09/887,145

(22) Filed: Jun. 22, 2001

(65) Prior Publication Data

US 2003/0082139 A1 May 1, 2003

Related U.S. Application Data

(63) Continuation-in-part of application No. 09/855,468, filed on May 15, 2001, now abandoned, and a continuation-in-part of application No. PCT/US00/18777, filed on Jul. 10, 2000.

(51) Int. Cl.[7] .......................... C12N 5/02; C12N 5/06; C12N 5/08; C12N 15/86
(52) U.S. Cl. ...................... 435/325; 435/363; 435/366; 435/368; 435/456; 435/458
(58) Field of Search ................................ 435/456, 458, 435/325, 368, 363, 366

(56) References Cited

U.S. PATENT DOCUMENTS 5,762,926 A * 6/1998 Gage et al. .............. 424/93.21

OTHER PUBLICATIONS

Briers et al. (Jul. 1994) "Generation and characterization of mouse microglial cell lines." Journal of Neuroimmunology 52(2): 153–164.*

Fontijn et al. (Jan. 19, 1999) "Maintenance of Vascular Endothelial Cell–Specific Properties after Immortalization with an Amphotrophic Replication–Deficient Retrovirus . . . " Experimental Cell Research 216(1): 199–207.*

Janabi et al. (Aug. 16, 1996) "Establishment of human microglial cell lines after transfection of primary cultures of embryonic microglial cells with the SV40 large T antigen." Neuroscience Letters 195(2): 105–108.*

Hosaka et al. (Jul. 20, 1992) "Generation of microglial cell lines by transfection with simian virus 40 large T gene." Neuroscience Letters 141(2): 139–142.*

* cited by examiner

Primary Examiner—Gary Kunz
Assistant Examiner—Christopher James Nichols
(74) Attorney, Agent, or Firm—David Prashker

(57) ABSTRACT

An immortalized human cell line is provided which has the characteristics of human embryonic microglia. Such immortalized microglia cells express CD68, CD11c and MHC class I and II antigens as surface markers; have demonstrable phagocytic properties; and produce progeny continuously while maintained in culture. A method of transforming human microglial cells into an immortalized cell line is also provided. The genetically modified human microglia cells can express active substances from a selected group consisting of MIP-1β, MCP-1, IL-1β, IL-6, IL-12, and IL-15; and in the stimulated state can overexpress at lest cytokines, chemokines, and other cytotoxic and neurotoxic substances. Such immortalized microglia cells can be used for screening of compounds for diseases. These cells may be utilized for the treatment of at least Alzheimer disease, Parkinson disease, Huntington disease, amyotrophic lateral sclerosis, stroke, spinal cord injuries, ataxia, autoimmune diseases and AIDS-dementia.

10 Claims, 6 Drawing Sheets

1) Control
2) Aβ (20 μM)
3) LPS (100 ng/ml)

HMO6 46XY

SEQUENCE LISTING (1) GENERAL INFORMATION:

(iii) NUMBER OF SEQUENCES: 55

(2) INFORMATION FOR SEQ ID NO: 1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 1:

AGATTCGAGT CATGTACACA ACCCA                                              25

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 2:

GGTGCTTGGA GATCTCGAAG                                                    20

(2) INFORMATION FOR SEQ ID NO: 3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 3:

TGTGGTGTAC CCCCTCAAGT CCC                                                23

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 4:

ATCCGTAACA GCCCAGAATC AGCA                                               24

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: peptide -continued (xi) SEQUENCE DESCRIPTION: SEQ ID NO: 5:

CCAGGCCCCC GTGCTCTACT TTG                                       23

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 6:

CATGTTGATG GCGTTGAGGG TGTG                                      24

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 7:

TTCTACCCCA ATGACTTGTG                                           20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 8:

ATGTAGTAAG GCAGCCAACA                                           20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 9:

ACCATGGCTC TCTGCAACCA                                           20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 10:

TTAAGAAGAG TCCCACAGTG                                           20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 11:

CCTGCTGCTT TTCTTACACC                                                      20

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 12:

CACCTAATAC AATAACACGG C                                                  21

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 13:

ATAGCAGCCA CCTTCATTCC                                                      20

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 14:

TTCCCCAAGT CTCTGTATCT                                                      20

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 15:

AAAAGCTTGG TGATGTCTGG                                                      20

(2) INFORMATION FOR SEQ ID NO: 16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 16:

TTTCAACACG CAGGACAGG                                     19

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 17:

ATGGTTGCTG TCTCATCAGC                                   20

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 18:

CTGGAGCATT TACTGCTGGA                                   20

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 19:

ATGAGCCGCC TGCCCGTCCT G                                   21

(2) INFORMATION FOR SEQ ID NO: 20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 20:

AAGATCGCGA GGCTCAAAGT CGTCTGTTG                            29

(2) INFORMATION FOR SEQ ID NO: 21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 21:

```
GACACAAGTG CAATATCACC                                          20
```

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 22:

```
AAGTTTTCCA ACGTACTCTG                                          20
```

(2) INFORMATION FOR SEQ ID NO: 23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 23:

```
GAGGATGCTT CTGCATTTGA GTTTG                                    25
```

(2) INFORMATION FOR SEQ ID NO: 24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 24:

```
GTCAATGTAT TTCTTTATTA AGGACAAG                                 28
```

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 25:

```
GTGTGAAAGC AGCAAAGAGG C                                        21
```

(2) INFORMATION FOR SEQ ID NO: 26:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: peptide (xi) SEQUENCE DESCRIPTION: SEQ ID NO: 26:

CTGGAGGTAC TCTAGGTATA C                                              21

(2) INFORMATION FOR SEQ ID NO: 27:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: peptide (xi) SEQUENCE DESCRIPTION: SEQ ID NO: 27:

TGTTGAACTG CACTGGCCAG                                                20

(2) INFORMATION FOR SEQ ID NO: 28:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: peptide (xi) SEQUENCE DESCRIPTION: SEQ ID NO: 28:

GCAACTGATA CCTTACATGG                                                20

(2) INFORMATION FOR SEQ ID NO: 29:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: peptide (xi) SEQUENCE DESCRIPTION: SEQ ID NO: 29:

ATGACTTCCA AGCTGGCCGT G                                              21

(2) INFORMATION FOR SEQ ID NO: 30:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: peptide (xi) SEQUENCE DESCRIPTION: SEQ ID NO: 30:

TATGAATTCT CAGCCCTCTT CAAAA                                          25

(2) INFORMATION FOR SEQ ID NO: 31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 31:

ATGCTTCTGG CCATGGTCCT                                                     20

(2) INFORMATION FOR SEQ ID NO: 32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 32:

TATCTTGCCT CTCATCCCTC                                                     20

(2) INFORMATION FOR SEQ ID NO: 33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 33:

AGATCTCCGA GATGCCTTCA GCAGA                                         25

(2) INFORMATION FOR SEQ ID NO: 34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 34:

CCTTGATGTC TGGGTCTTGG TTCTC                                         25

(2) INFORMATION FOR SEQ ID NO: 35:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 35:

ACTGCTGCTG CTGAAGACTC GGCTGTGA                                   28

(2) INFORMATION FOR SEQ ID NO: 36:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 36:

ATGGGGAAGA GCCAGGGCAG AAGTCTGT         28

(2) INFORMATION FOR SEQ ID NO: 37:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 37:

TCACAAAGGA GGCGAGGTTC TAAGC         25

(2) INFORMATION FOR SEQ ID NO: 38:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 38:

CCTCTGCTGC TTTTGACACT GAATG         25

(2) INFORMATION FOR SEQ ID NO: 39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 39:

ACCCAGAACC AGAAGGCTCC G         21

(2) INFORMATION FOR SEQ ID NO: 40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 40:

TCAGTTGAAC CGTCCCTGGC G         21

(2) INFORMATION FOR SEQ ID NO: 41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 41:

AAACCCCCTG CCATAGCCAA CTCTT                                          25

(2) INFORMATION FOR SEQ ID NO: 42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 42:

CTTCTGTTTT AGGGAGCCCT GCACT                                          25

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 43:

CAAAGTAGAC CTGCCCAGAC                                                      20

(2) INFORMATION FOR SEQ ID NO: 44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 44:

GACCTCTCTC TAATCAGCCC                                                      20

(2) INFORMATION FOR SEQ ID NO: 45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 45:

TGGGAAATGG CTCGTCATTT                                                      20

(2) INFORMATION FOR SEQ ID NO: 46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 46:

CTTCATGGAA GCGGCCAATT                                            20

(2) INFORMATION FOR SEQ ID NO: 47:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 47:

ACACGGGCAT CCTTGACTCC ATCGG                                  25

(2) INFORMATION FOR SEQ ID NO: 48:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 48:

TCCGGAACCA GGTGGGTTTT CAGCG                                  25

(2) INFORMATION FOR SEQ ID NO: 49:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 49:

GCAGAGATGA TGGAGCTCAA TGACC                                  25

(2) INFORMATION FOR SEQ ID NO: 50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 50:

GTTTCATCCT GGAGCTTCTG CCTCA                                  25

(2) INFORMATION FOR SEQ ID NO: 51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 51:

```
CTCTTTGTGA TGGCCTTCCT G                                      21
```

(2) INFORMATION FOR SEQ ID NO: 52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 52:

```
CTTAGGTTCT GGGTAACCGT G                                      21
```

(2) INFORMATION FOR SEQ ID NO: 53:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 53:

```
CCATGTTCGT CATGGGTGTG AACCA                                  25
```

(2) INFORMATION FOR SEQ ID NO: 54:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 54:

```
GCCAGTAGAG GCAGGGATGA TGTTC                                  25
```

(2) INFORMATION FOR SEQ ID NO: 55:

(i) SEQUENCE CHARACTERISTICS:
        (A) LENGTH: 11 residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 55:

```
Gly Ser Asn Lys Gly Ala Ile Ile Gly Leu Met
1               5                   10
```

IMMORTALIZED HUMAN MICROGLIA CELL LINE

CROSS-REFERENCE

This application is a Continuation-In-Part of U.S. patent application Ser. No. 09/855,468 filed May 15, 2001, now abandoned and of International Patent Application No. PCT/US00/18777 having an international filing date of 10 Jul. 2000, now pending.

RESEARCH SUPPORT

The research for the present invention was supported in part by grants from the Multiple Sclerosis Society of Canada and the Canadian Myelin Research Initiative.

FIELD OF THE INVENTION

The present invention is concerned generally with glial cell components of the central nervous system; and is particularly directed to in-vitro isolation of embryonic human microglia ("HM") cells and establishment of immortalized human microglia ("HMO6") cells and cell lines which are identifiable, stable, functionally active, and in continuous proliferation in-vitro.

BACKGROUND OF THE INVENTION

Microglia are a major glial component of the central nervous system (CNS); play a critical role as resident immunocompetent cells and phagocytic cells in the CNS [van Furth, R., Immunobiol. 161: 155–185 (1982)]; and serve as scavenger cells in the event of infection, inflammation, trauma, strokes, autoimmune disease, and neurodegeneration in the CNS [Kreutzbeng, G. W., Trends Neurosci. 19: 312–318 (1996); El Khoury et al., Neurobiol. Aging 19: 581–584 (1998); Thomas W. E., Brain Res. Rev. 17: 61–74 (1992)]. Activated microglia are observed in pathological lesions in several neurological diseases, including neurodegenerative diseases [McGeer et al., Glia 7: 84–92 (1993)]; autoimmune CNS diseases [Boyle, E. K. and P. L. McGeer, Am. J. Pathol. 137: 575–584 (1990)]; and acquired immune deficiency syndrome dementia complex (AIDS-DC) [Gelman, B. B., Ann. Neurol. 34: 65–70 (1993)].

Microglia were first described in 1932 by Rio-Hortega [Rio-Hortega, P. D., In *Cytology and Cellular Pathology of Nervous System*, Vol. 2 (W. Penfield, ed.), Paul B. Hoeber, N.Y., 1932, p. 481–534] in silver carbonate stained brain preparations at the light microscope level as a morphologically distinct cell type with long and branched processes. On the basis of studies in developing CNS using silver staining or electron microscopy, microglia cells have at various times been described as mesodermal, monocytic or ecodermal in origin [Ashwell, K., *J. Comp. Neurol.* 287: 286–301 (1959); Hickey, W. F. and H. Kimura, *Science* 239: 292—292 (1988); Kitamura et al., *J. Comp. Neurol.* 226: 421–433 (1984); and Sminia et al., *Immunobiol.* 174: 43–50 (1987)].

The prevailing concept in this field is that fetal monocytes (which later differentiate into macrophage) enter the brain and retina during embryonic development; and subsequently differentiate into microglia. For that perceived reason, many cell surface antigens are demonstrably shared between adult microglia and adult macrophages. These commonly shared antigens include CD11b (Mac-2, β2 integrins), CD11c (LeuM5), CD45 (leukocyte common antigen), CD64 (Fc γ receptor), CD68 (macrophage antigen), complement type 3 receptor (CR3) and the major histocompatibility complex (MHC) class I and II antigens [Kreutzberg, G. W., *Trends Neurosci.* 19: 312–318 (1992); McGeer et al., *Glia* 7: 84–92 (1993)]. It is recognized that during inflammatory reactions, MHC class-II antigens induction in microglia are widespread in the CNS. Thus, the MHC antigen HLA-DR is a consistent marker for activated microglia.

When microglia activation occurs in response to neuronal injury, the activated microglia transforms into phagocytic cells capable of releasing several potentially cytotoxic substances, such as oxygen radicals, nitric oxide, proteases, and proinflammatory cytokines [Banati et al., *Glia* 7: 111–118(1993); Banati et al., *Glia* 7: 183–191 (1993); Colton et al., *FEBS Lett.* 223: 284–288 (1987); Dickson et al., *Glia* 7: 75–83 (1993)]. Among the proinflammatory cytokines produced by activated microglia are interleukin-1 (IL-1), tumor necrosis factor-α (TNF-α), and IL-6—all of which are able to induce cytotoxic effects or cytopathic effects in the CNS.

Thus, recent studies have indicated that activation of microglia either precedes or is concomitant with neuronal and glial cell degeneration in neurological diseases including amyotrophic lateral sclerosis (ALS), Alzheimer disease (AD), Parkinson disease, stroke, brain trauma, AIDS-DC and multiple sclerosis. Amyloid β protein 1–42 fragments ($A\beta_{1-42}$) (which accumulate in senile plaques of AD brain) have been shown to be neurotoxic and to trigger production of reactive oxygen species and nitrogen intermediates as well as proinflammatory cytokines—as demonstrated in rat microglial cells and human monocytes exposed to the peptide [Araujo et al., *Brain Res.* 569: 141–145 (1992); Klegeris et al., *Biochem. Biophys. Res. Commun.* 199: 984–991 (1994); Meda et al., *Nature* 374: 647–650 (1995); Meda et al., *Neuroimmunol.* 93: 45–52 (1999); Goodwin et al., *Brain Res.* 692: 207–214 (1995)]. The Aβ 25–35 fragments ($A\beta_{25-35}$) are identified as the active fragments of amyloid β protein, reproducing both the neurotoxic effect and the production of proinflammatory effects induced by $A\beta_{1-42}$ [Yanker et al., *Brain Res.* 653: 243–250 (1994)].

Microglia-mediated neurotoxicity also appears to be critical in tissue damage and neuronal death during the initiation and progression of the AD disease process. Many expected studies on human microglia have been performed using histological sections while more recent work uses primary cultures of fetal cells or adult brain tissue. However, all these studies have had serious limitations in obtaining sufficient human microglia in order to study in detail the cellular and molecular characteristics of this cell type.

There is, therefore, a long existing and well recognized need in this art for stable, continuous cell lines of human microglia. The generation of such cell lines would permit the first essential elucidation and description of the phenotypic expression for human microglia in detail; and would also offer a stable line of human microglia cells for an in-depth examination of cytokine and chemokine expression.

SUMMARY OF THE INVENTION

The present invention has multiple aspects. A primary aspect of this invention provides a genetically modified human microglia cell maintained as a stable cell line in-vitro comprising:

a modified microglia cell of human origin which
(i) has demonstrable phagocytic properties;
(ii) produces progeny continuously while maintained in culture;
(iii) presents at least CD11b and CD68 as surface antigens; and (iv) contains human genomic DNA which has been genetically modified to include a viral vector carrying at least one DNA segment encoding an exogenous gene for intracellular expression.

BRIEF DESCRIPTION OF THE FIGURES

The present invention may be more easily understood and better appreciated when taken in conjunction with the accompanying drawing, in which.

DETAILED DESCRIPTION OF THE INVENTION

Figure 1:
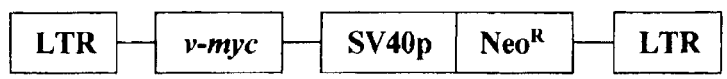
FIG. 1 is a schematic illustration showing the construction of a retroviral vector used to generate the immortalized human microglia cell line.

The present invention is the establishment and characterization of several continuous cell lines of immortalized human microglia, labeled as HMO6, generated by transfection of embryonic (fetal) human microglia (HM) with a retroviral vector containing cDNA for the v-myc oncogene. The invention provides a phenotypic characterization of these immortalized human microglia; and discloses the expression of cytokines and chemokines following exposure to β amyloid peptides using HM and HMO6 cells. For a clearer understanding and better appreciation of the subject matter as a whole which comprises the present invention, the detailed description will be presented as separate sections.

I. A Preferred Method for Producing Immortalized Human Microglia Cells and Continuous Cell Lines 'Human microglial cell line, as used herein, means a human-derived cell line with microglial characteristics, including at least the specific antigens CD68 and CD11b. Also, as used herein, "non-fetal" refers to the fact that the progeny cells are expanded from immortalized cells in-vitro, and there is no need to return to an embryonic/fetal source for additional microglia cells.

Vectors

It should be understood that a number of different vectors besides the retroviral vector described herein can be used to transform embryonic human microglia (HM) cells. The transformation of such embryonic HM cells is conventionally known and routinely performed within the art; and HM cells transformed by any other vector can be prepared as disclosed below and subsequently tested to assure the presence of identifying microglial phenotypic markers. Further, the vectors are not limited to immortalizing HM cells with the oncogene v-myc. Many other varieties of oncogenes are known in the art and are suitable for immortalizing embryonic human microglia.

General Methods

Standard molecular biology techniques known in the art and not specifically described herein are generally followed as in Sambrook et al., *Molecular Cloning, A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) is carried out generally as in *PCR Protocols: Guide to Methods and Applications*, Academic Press, San Diego, Calif. (1990). Reactions and manipulations involving other nucleic acid techniques, unless stated otherwise, are performed as generally described in Sambrook et al., 1989, *Molecular Cloning: A Laboratory Manual*, Cold Springs Harbor Laboratory Press, and the methodology set forth in U.S. Pat. Nos. 4,666,828; 4,683,202; 4,801,531; 5,192,659; and 5,272,057 and incorporated herein by reference. In-situ PCR in combination with Flow Cytometry can be used for detection of cells containing specific DNA and mRNA sequences [Testoni et al., *Blood* 87: 3822 (1996)].

Standard methods in immunology known in the art and not specifically described herein are generally followed as in Stites et al., *Basic and Clinical Immunology*, 8th Ed., Appleton & Lange, Norwalk, Conn. (1994); and Mishell and Shigi (eds.), *Selected Methods in Cellular Immunology*, W. H. Freeman and Co., New York (1980).

Human Microglia Culture

Brain tissue (mostly telencephalon) is obtained from 12–18 weeks gestation embryos. The brain tissue is incubated in phosphate buffered saline (PBS) containing 0.25% trypsin and 40 ug/ml DNase for 30 min. at 37° C. and then dissociated into single cells by gentle pipetting. Dissociated single cells are then preferably grown in a feeding medium consisting of Dulbecco's modified Eagle's medium (DMEM) to which the following are added: 5% horse serum, 5 mg/ml D-glucose and 20 ug/ml gentamicin. After 2–3 weeks of growth in flasks, free-floating microglia can be collected and plated in 6-well plates coated with poly-L-lysine.

It is also desirable that, for the last part of this time, microglia are exposed to granulocyte macrophage colony stimulating factor (GM-CSF) at final concentration of 8 ug/ml for 9–12 days with a medium change every 3 days. GM-CSF treatment stimulated proliferation of microglia results in a 3–4 fold increase in microglial population.

The human microglia isolated from primary cultures of embryonic human telencephalon brain cells are mostly round cells, with filopodia surrounding the cell bodies, or appear as slender cells having several primary branches. The cells typically are from 8–12 um in size. Human microglia composed in excess of 98% of plated cells (as determined using the specific cell type-specific marker, ricinus communis agglutinin-1 and CD11b).

Retrovirus-Media Gene Transfer

Embryonic human microglia grown with GM-CSF for 9–12 days are then subjected to retrovirally mediated transduction of v-myc and subsequent cloning. An amphotropic replication-incompetent retroviral vector encoding v-myc oncogene transcribed from mouse leukemia virus LTR plus neomycin-resistant gene transcribed from an internal SV40 early promoter is preferred for use to infect human microglia and induce propagation of immortalized human microglia cell lines. This amphotropic vector, PASK 1.2, was generated using the ecotropic retroviral vector encoding v-myc [obtained from the American Type Culture Collection (ATCC), Rockville, Md.] to infect the PA317 amphotropic packaging line.

Transfection

Successful infectants were then selected and expanded. Transfection of embryonic human microglia in 6-well plates is preferably performed by the following procedures: 2 ml of supernatant from the PA317 packaging line and 8 ug/ml polybrene is added to microglia in 6-well plates and incubated for 4 hr at 37° C.; the solution is then replaced with fresh feeding medium; and transfection repeated 24 hr later. After 72 hr, the transfected cells are selected with neomycin (G418). Individual clones are generated by limiting dilution and propagated further.

In this manner, several neomycin (G-418) resistant colonies were isolated, expanded and were named HMO6. One of these HMO6 cell lines, the HMO6.A1 cell line, has been investigated for its cellular and molecular characteristics, as presented hereinafter. The terms "HM06" and "HM06.A1" are therefore synonymous and are used interchangeably hereinafter.

II. Characteristics and Properties of Immortalized Human Microglia Cells

The HMO6 human microglia cell and cell line is presented as a typical representation and illustrative example of the immortalized cells constituting the present invention. For these reasons, the detailed description will focus upon and be limited to characterizing the attributes of the HMO6 cell.

Surface Antigens

An immunohistochemical study (presented in detail by the Experiments described hereinafter) utilized a range of antibodies to identify those surface antigens which are expressed by the immortalized microglia cells. A summary listing of such surface markers is given by Table 1 below.

TABLE 1

Cell Type-Specific Markers For CNS Cells

| Antigen | Identifying Specificity | HMO6 |
| --- | --- | --- |
| Human mitochondria | mitochondria | + |
| Pan-myc | myc | + |
| RCA-1 lectin | microglia | ++ |
| CD11b | microglia | + |
| CD68 | microglia | + |
| HLA-ABC | MHC class I | + |
| HLA-DR | MHC class II | + |
| MAP-2 | neuron | − |
| β tubulin III | neuron | − |
| GFAP | astrocytes | − |
| MBP | oligodendrocytes | − |

Antigen reactivity were determined by immunohistochemistry. Immunoreactivity was expressed in a scale ranging from − (negative) to ++ (strong positive).

As the data of Table 1 shows, HMO6 cells expressed surface antigens specific for microglia cells such as CD11b, CD68, HLA-ABC, HLA-DR, and ricinus commuriis agglutinin-1 lectin (RCA-1) as determined by immunocytochemistry (Antibody source: DAKO Diagnostics Canada, Inc., Mississauga, Ontario).

Phagocytic Capacity

When HMO6 cells were exposed for two hours to medium containing latex beads (0.8 um size, Sigma) at the ratio of 1 μl per 1 ml medium or to medium containing carbon particles (prepared from Chinese ink stick) at 37° C., all cells became loaded with latex beads or carbon particles. This demonstrates that the HMO6 cells are capable of active phagocytosis, one of the most significant function and features characterizing microglia-macrophage lineage cells of the CNS.

Chemokine and Cytokine Expression

To determine if and what pharmacologically active molecules are expressed and produced by HMO6 cells in a non-stimulatory condition (i.e., without addition of or reactive contact with active stimulating agents such as TNF-α, LPS, and the like), a series of RT-PCR analyses were performed. Detailed description of such RT-PCR analyses themselves is provided by the Experiments hereinafter. The results of these analyses, however, are listed in summary form by Table 2 below.

TABLE 2

RT-PCR Analysis of Non-Stimulated HMO6 Cells

| | |
| --- | --- |
| Constitutive marker/expression of IL-1b | + |
| Constitutive marker/expression of IL-6 | + |
| Constitutive marker/expression of IL-8 | + |
| Constitutive marker/expression of IL-12 | + |
| Constitutive marker/expression of IL-15 | + |
| Constitutive marker/expression of TNF-α | −* |
| Constitutive marker/expression of MIP-1α | −* |
| Constitutive marker/expression of MIP-1β | + |
| Constitutive marker/expression of MCP-1 | + |

*Expression of TNF-α and MIP-1α was induced by treatment with TNF-α or Aβ.

In comparison, HMO6 cells can be stimulated using a variety of active agents. A summary of the expressed active molecules generated by specific stimulating agents is given by Table 3 below.

TABLE 3

RT-PCR Analysis Of Agent Stimulated HMO6 Cells

| Stimulating agent | Stimulated HMO6 cell expressed active substance(s) |
| --- | --- |
| TNF-α | TNF-α |
|  | MIP-1α |
| IL-1β | None |
| LPS | IL-8 |
|  | IL-12 |
|  | MIP-1β |
|  | $P_{2y2}$ |
| Aβ$_{25-35}$ | TNF-α |
|  | Elevated IL-12 |
| CXCR4 | $P_{2y2}$ |
| IFN-γ | $P_{2y2}$ |
|  | B7-2 |

III. Expected and Intended in-vitro Assay Uses and in-vivo Therapeutic Uses for the Immortalized Human Microglia Cells It has been long recognized that microglia play a critical role as resident immunocompetent cells and phagocytic cells in the central nervous system (CNS) and serve as scavenger cells in the event of infection, inflammation, trauma, ischemia and neurodegeneration in the CNS. Activated microglia have been observed in pathological lesions in neurodegenerative diseases and are believed to be involved in initiation or progression of CNS pathology. Neurodegeneration is often preceded or is concomitant with the functional responses of microglia in-vivo, including cell proliferation and the secretion of active molecules including oxygen radicals, proteases and pro-inflammatory cytokines.

Moreover, recent studies have indicated that the activation of native microglia precedes or is concomitant with neuronal and glial cell degeneration in a variety of neurological diseases, including amyotrophic lateral sclerosis (ALS), Alzheimer disease (AD), Parkinson disease, Huntington disease (HD), stroke, brain trauma, AIDS-dementia, and multiple sclerosis. Thus, microglia-mediated neurotoxicity appears to be critical in tissue damage and neuronal death during the initiation and pathological progression of neurological disorders, in-vivo.

In addition, recent experimental studies reported by others indicate that murine microglia cells produce neurotrophic factor(s) that promote survival of CNS neurons in an environment in which majority of neurons undergo degeneration in the absence of microglia conditioned medium. Previous studies have also indicated that murine/human microglia cells in culture produce neurotoxic substance following exposure to β-amyloid for 24–48 hours.

For these reasons, a variety of in-vitro assays and in-vivo therapeutic uses are envisioned and intended for the present invention. These include the following:

1. The immortalized human microglia cells can be used in-vitro to isolate neurotoxic or neurotrophic molecules naturally produced by human microglia or produced in response to inflammatory factors or neuroactive molecules such as β-amyloid.
2. Because microglia have been implicated in neurological disorders, such as Alzheimer disease, Parkinson disease, AIDS-dementia, ALS and MS, the immortalized human microglia can be used for discovery (screening) of new drugs to treat the aforementioned conditions and inflammation. Prospective drug candidates are those that can counter or reduce production of proinflammatory cytokines, oxygen radicals, proteases such as caspase-3 and -8, and neurotoxic agents such as β-amyloid.
3. Human immortalized microglial cells can be further genetically manipulated to express and produce additional proteins, peptides, or prodrugs. Such substances would include a diverse range of chemokines, cytokines, and various marker proteins (e.g., LacZ and GFP), growth factors, neurotrophic molecules, anti-apoptotic molecules (e.g., Bcl-2), and enzyme inhibitors (e.g., caspase inhibitor). Microglia cells can be additionally genetically modified to block the production of proteins that typically become overproduced by nervous system pathologies. For example, upstream from the v-myc gene, there can be inserted an activatable suppressor gene. Alternately, for human treatment, there can be inserted a suicide gene.
4. Microglia cells are known to be activated by inflammatory factors/cytokines/chemokines in neurodegerative diseases including Alzheimer disease, Parkinson disease, Huntington disease and ALS, and stroke. In Alzheimer disease, nonsteroidal anti-inflammatory drug (NSAID) such as indomethacin has been reported to delay progression of disease process by blocking/inhibiting microglial activities. For that reason, human immortalized microglia cells could be utilized for screening drugs which can block or suppress microglial activation and progression of disease process.
5. It has been observed that murine microglia cells introduced via venous injection could translocate into brain parenchyma. It is well known that external molecules or cell elements can not pass barrier called blood-brain-barrier (BBB) and enter into brain proper. For that reason, microglia cells capable of bypassing BBB could deliver drugs into brain without difficulty. One can also genetically engineer immortalized human microglia cells to carry desired gene to produce proteins and/or prodrugs and then introduced into patients brain. This is a novel and useful way of drug delivery system.

In the expected therapeutic methods of the present invention, the immortalized human microglia can be administered in various ways as would be appropriate to implant in the central nervous system, including but not limited to parenteral administration, intrathecal administration, intraventricular administration, and intranigral administration.

In each envisioned and intended in-vivo context, and particularly with the therapeutic treatment of neurodegenerative diseases and disorders, the cells of the present invention are to be administered and implanted in accordance with accepted good medical practices. Such good medical practices take into account the clinical condition of the individual patient; the site and method of administration; scheduling of administration; and patient age, sex, body weight and other personal factors known to medical practitioners. The pharmaceutically "effective amount" for purposes herein is thus determined by such medical considerations as are known in the art. The cell amount must be sufficient to achieve clinical improvement, including (but not limited to) improved survival rate or more rapid recovery; and improvement or elimination of clinical symptoms and other medical indicators as are recognized by those skilled in the medical arts.

IV. Experiments and Empirical Data

To demonstrate the merits and value of the present invention, a series of planned experiments and empirical data are presented below. It will be expressly understood, however, that the experiments described and the results provided below are merely the best evidence of the subject matter as a whole which is the present invention; and that the empirical data, while limited in content, is only illustrative of the scope of the invention as envisioned and claimed.

METHODS AND MATERIALS

Abbreviations Used

AIDS-DC, acquired immune deficiency syndrome dementia complex; Aβ, amyloid-β protein; AD, Alzheimer disease; CNS, central nervous system; ELISA, enzyme-linked immunosorbent assay; HM, embryonic human microglial cells; IL, interleukin; LPS, lipopolysaccharide; RT-PCR, reverse transcription-polymerase chain reaction; TNF-tumor necrosis factor alpha; IFN-, interferon-gamma, LTR, long-term repeat $GM_R$-CSF, granular monocytes-cebebral spinal fluid; PBS, phosphate buffered saline; DMEM, Delbeccio's Minimal Eagle Media; SEM, scanning electron micrograph; ABC; avidin biotin complex.

Reagents

The following reagents were used in the present study: Recombinant human IL-1β and TNF-α (10 ng/ml, R&D Systems, Minneapolis, Minn.), recombinant human IFN-γ (500 IU/ml, LG Chem, Taejon, Korea), granulocyte-macrophage colony-stimulating factor (GM-CSF, 10 ng/ml, GIBCO-BRL), lipopolysaccharide (LPS) and $Aβ_{25-35}$ (Sigma, St. Louis, Mo.).

Primary Microglial Cell Culture

Primary microglial cell cultures were isolated from embryonic human brains of 12–15 weeks' gestation, as described previously [Satoh, J. and S. U. Kim, *Brain Res.* 65: 243–250 (1994); Satoh, J. and S. U. Kim, *J. Neurosci. Res.* 39: 260–272 (1994); Satoh, J. and S. U. Kim, *J. Neurosci. Res.* 37: 466–474 (1994)]. The permission to use embryonic tissue was granted by the Ethics Committee of the University of British Columbia. In brief, the embryonic brains were dissected into small blocks and incubated in phosphate-buffered saline (PBS) containing 0.25% trypsin and 40 $\mu$g/ml Dnase I for 30 min at 37° C. Dissociated cells were suspended in Dulbecco's modified Eagle medium (DMEM) supplemented with 5% horse serum, 5 mg/ml D-glucose, 25 $\mu$g/ml streptomycin and 2.5 g/ml amphotericin B (feeding medium), plated at a density of $10^6$ cells/ml in T75 culture flasks, and incubated at 37° C. in an incubator with 5% $CO_2$/95% air atmosphere.

After 2–3 weeks in-vitro, microglia-enriched cultures were prepared by harvesting the floating cells in flasks and replated on gelatin-coated 6-well plates ($2\times10^5$ cells/well) for retrovirus-mediated gene transfer or plated on poly-L-lysine (PL) coated 9 mm Aclar plastic round coverslips ($2\times10^4$ cells/coverslip) for immunocytochemistry. Microglia were found in excess of 99% of plated cells as determined using cell type-specific markers, Ricinus communis aggulutin-1 (RCA-1 lectin) and CD11b. Culture medium was changed twice a week.

Retrovirus-Mediated Gene Transfer

As illustrated by FIG. 1, an amphotropic replication-incompetent retroviral vector encoding v-myc oncogene (transcribed from mouse leukemia virus LTR plus neomycin-resistant gene transcribed from a SV40 early promotor) was used to infect human microglia inducing propagation of immortalized human microglial cell lines. This amphotropic vector, PASK 1.2, was generated using the ecotropic retroviral vector encoding v-myc (obtained from the American Type Culture Collection, Rockville, Md.) to infect PA318 amphotropic packaging cell line. Microglia were exposed to granulocyte macrophage colony stimulating factor (GM-CSF) at final concentration of 8 $\mu$g/ml for 9–12 days with medium change every 3 days. GM-CSF treatment stimulated proliferation of microglia resulting in 3–4 folds increase in population. Microglia treated with GM-CSF for 9–12 days were subjected to retrovirally mediated transduction of v-myc by PASK 1.2 construct and subsequent cloning.

Successful infectants were selected and expanded. Infection of human microglial cells in 6 well plates was performed three times by the following procedures: 2 ml of supernatant ($4\times10^5$ CFUs) from the packaging cell line and 8 $\mu$g/ml polybrene (Aldrich/Sigma) was added to target cells in 6 well plates and incubated for 4 hr at 37° C.; the medium was then replaced with fresh growth medium; infection was repeated 24 hr and 48 hr later.

Seventy two hours after the third infection, infected cells were selected with neomycin (G418; 250 $\mu$g/ml, Sigma) for 7–14 days and large clusters of clonal cells were individually isolated and grown in PL-coated 6 well plates. Individual clones were generated by limited dilution and propagated further. At this phase of isolation, the individual clones were designated as human microglial cell lines, HMO6. One of these clones, HMO6.A1, was subjected to further study.

Methods for Characterization of Human HMO6 Cells

Phagocytosis of Latex Beads

The phagocytic abilities of HMO6.A1 cells were tested using the following assay technique. Latex beads (0.8-$\mu$m size, Sigma) were added to wells containing cultured cells at 1-$\mu$l beads/ml. After 2 hr incubation, the cultures were rinsed several times with PBS and fixed in 4% paraformaldehyde (in 0.1 M phosphate buffer). The phagocytosis of latex beads was examined under a Nikon phase contrast microscope.

Determination of Doubling Time

HMO6 cells at the concentration of $5\times10^4$ cells were plated in 30 mm dishes with 2 ml of medium. After 12–72 hours of growth, cells were exposed to 0.1% trypsin in PBS for 5 min at 37° C., collected by centrifugation at 1,200 rpm for 8 min, and resuspended in 0.5 ml PBS. Using a hemocytometer, cell number was counted 12, 24, 36, 48, 60 and 72 hr after plating under a Nikon inverted microscope.

Immunochemical Characterization

Immunochemical determination of cell type specific surface antigen markers in HMO6.A1 cells was performed as follows: HMO6.A1 cells were grown on PL-coated Aclar plastic coverslips (9 mm in diameter) in serum-free medium for 3–7 days, fixed in 4% paraformaldehyde in 0.1 M phosphate buffer (PB, pH 7.4) for 3 min at room temperature (RT), washed twice with PBS, and incubated with antibodies specific for each cell type. For cytoplasmic antigen staining, coverslips bearing cells were fixed in cold acid alcohol (5% acetic acid in 95% ethanol) for 15 min at −20° C. Fixed cultures were incubated with heat-inactivated normal goat serum in PBS (1:10) for 20 min at room temperature before the primary antibodies were applied, in order to block any potential interaction between Fc receptors and Fc fragments. Cultures incubated with primary antibodies were followed by biotinylated secondary antibodies and avidin-biotin complex (ABC) immunochemical processing (Vector) and visualized with 3-amino-9-ethyl carbazole (Sigma) chromogen development.

The anti-human antibodies utilized for immunochemical characterization of differentiated cell types are shown in Table E1.

Fura-2 $Ca^{2+}$-Fluorescence

The cultured HMO6.Al cells were loaded for 25 min with the $Ca^{2+}$ indicator fura-2-acetoxymetethylester (fura-2AM). The dye was applied with pleuronic acid (both at concentrations of 1 $\mu$M) to normal physiological solution (PSS) at room temperature (20–22° C.). Following a 5 min wash in dye-free solution, the coverslips were placed on the stage of a Zeiss Axiovert inverted microscope containing a ×40 quartz objective lens. Alternating excitation wavelengths (340/380 nm) of UV light were applied at intervals of 8 s and fluorescence signals were obtained at 510 nm of emission light (bandwidth of 4 nm) from 8–20 cells in the field of view. Signals were acquired from a digital camera (DVC-1310, DVC Co., Austin, Tex.) and were processed using an imaging system (Empix, Mississauga, ON) to determine ratios of the 340 nm and 380 nm intensities which have been used as quantitative measures of fluorescence levels in this work.

All studies were done at room temperature (20–22° C.) and values obtained from multiple cells are reported as mean ±SEM with statistical significance for $p \leq 0.05$ using the Student's t-test.

RT-PCR

RT-PCR was performed with oligonucleotide primers as listed in Table E1 below. The information of Table E1 is provided merely as a convenience to the reader and utilizes conventional gene sequences.

TABLE E1

Sequences of PCR Primers

| Gene | | Sequence | | Product Size (bp) |
|---|---|---|---|---|
| CD68 | sense | AGATTCGAGTCATGTACACAACCCA | [SEQ ID NO:1] | 279 |
| CD68 | antisense | GGTGCTTGGAGATCTCGAAG | [SEQ ID NO:2] | |
| $P_{2Y1}R$ | sense | TGTGGTGTACCCCCTCAAGTCCC | [SEQ ID NO:3] | 260 |
| $P_{2Y1}R$ | antisense | ATCCGTAACAGCCCAGAATCAGCA | [SEQ ID NO:4] | |
| $P_{2Y2}R$ | sense | CCAGGCCCCCGTGCTCTACTTTG | [SEQ ID NO:5] | 367 |
| $P_{2Y2}R$ | antisense | CATGTTGATGGCGTTGAGGGTGTG | [SEQ ID NO:6] | |
| CXCR4 | sense | TTCTACCCCAATGACTTGTG | [SEQ ID NO:7] | 206 |
| CXCR4 | antisense | ATGTAGTAAGGCAGCCAACA | [SEQ ID NO:8] | |
| MIP-1α | sense | ACCATGGCTCTCTGCAACCA | [SEQ ID NO:9] | 393 |
| MIP-1α | antisense | TTAAGAAGAGTCCCACAGTG | [SEQ ID NO:10] | |
| MIP-1β | sense | CCTGCTGCTTTTCTTACACC | [SEQ ID NO:11] | 336 |
| MIP-1β | antisense | CACCTAATACAATAACACGGC | [SEQ ID NO:12] | |
| MCP-1 | sense | ATAGCAGCCACCTTCATTCC | [SEQ ID NO:13] | 466 |
| MCP-1 | antisense | TTCCCCAAGTCTCTGTATCT | [SEQ ID NO:14] | |
| IL-1β | sense | AAAAGCTTGGTGATGTCTGG | [SEQ ID NO:15] | 179 |
| IL-1β | antisense | TTTCAACACGCAGGACAGG | [SEQ ID NO:16] | |
| IL-2 | sense | ATGGTTGCTGTCTCATCAGC | [SEQ ID NO:17] | 301 |
| IL-2 | antisense | CTGGAGCATTTACTGCTGGA | [SEQ ID NO:18] | |
| IL-3 | sense | ATGAGCCGCCTGCCCGTCCTG | [SEQ ID NO:19] | 459 |
| IL-3 | antisense | AAGATCGCGAGGCTCAAAGTCGTCTTG | [SEQ ID NO:20] | |
| IL-4 | sense | GACACAAGTGCAATATCACC | [SEQ ID NO:21] | 337 |
| IL-4 | antisense | AAGTTTTCCAACGTACTCTG | [SEQ ID NO:22] | |
| IL-5 | sense | GAGGATGCTTCTGCATTTGAGTTTG | [SEQ ID NO:23] | 295 |
| IL-5 | antisense | GTCAATGTATTTCTTTATTAAGGACAAG | [SEQ ID NO:24] | |
| IL-6 | sense | GTGTGAAAGCAGCAAAGAGGC | [SEQ ID NO:25] | 159 |
| IL-6 | antisense | CTGGAGGTACTCTAGGTATAC | [SEQ ID NO:26] | |
| IL-7 | sense | TGTTGAACTGCACTGGCCAG | [SEQ ID NO:27] | 484 |
| IL-7 | antisense | GCAACTGATACCTTACATGG | [SEQ ID NO:28] | |
| IL-8 | sense | ATGACTTCCAAGCTGGCCGTG | [SEQ ID NO:29] | 301 |
| IL-8 | antisense | TATGAATTCTCAGCCCTCTTCAAAA | [SEQ ID NO:30] | |
| IL-9 | sense | ATGCTTCTGGCCATGGTCCT | [SEQ ID NO:31] | 375 |
| IL-9 | antisense | TATCTTGCCTCTCATCCCTC | [SEQ ID NO:32] | |
| IL-10 | sense | AGATCTCCGAGATGCCTTCAGCAGA | [SEQ ID NO:33] | 194 |
| IL-10 | antisense | CCTTGATGTCTGGGTCTTGGTTCTC | [SEQ ID NO:34] | |
| IL-11 | sense | ACTGCTGCTGCTGAAGACTCGGCTGTGA | [SEQ ID NO:35] | 295 |
| IL-11 | antisense | ATGGGGAAGAGCCAGGGCAGAAGTCTGT | [SEQ ID NO:36] | |
| IL-12 | sense | TCACAAAGGAGGCGAGGTTCTAAGC | [SEQ ID NO:37] | 213 |
| IL-12 | antisense | CCTCTGCTGCTTTTGACACTGAATG | [SEQ ID NO:38] | |
| IL-13 | sense | ACCCAGAACCAGAAGGCTCCG | [SEQ ID NO:39] | 198 |
| IL-13 | antisense | TCAGTTGAACCGTCCCTGGCG | [SEQ ID NO:40] | |
| IL-15 | sense | AAACCCCCTGCCATAGCCAACTCTT | [SEQ ID NO:41] | 202 |
| IL-15 | antisense | CTTCTGTTTTAGGGAGCCCTGCACT | [SEQ ID NO:42] | |
| TNF-α | sense | CAAAGTAGACCTGCCCAGAC | [SEQ ID NO:43] | 490 |
| TNF-α | antisense | GACCTCTCTCTAATCAGCCC | [SEQ ID NO:44] | |
| NF-M | sense | TGGGAAATGGCTCGTCATTT | [SEQ ID NO:45] | 333 |
| NF-M | antisense | CTTCATGGAAGCGGCCAATT | [SEQ ID NO:46] | |
| MBP | sense | ACACGGGCATCCTTGACTCCATCGG | [SEQ ID NO:47] | 510 |
| MBP | antisense | TCCGGAACCAGGTGGGTTTTCAGCG | [SEQ ID NO:48] | |

TABLE E1-continued

Sequences of PCR Primers

| Gene | | Sequence | | Product Size (bp) |
|---|---|---|---|---|
| GFAP | sense | GCAGAGATGATGGAGCTCAATGACC | [SEQ ID NO:49] | 266 |
| GFAP | antisense | GTTTCATCCTGGAGCTTCTGCCTCA | [SEQ ID NO:50] | |
| B7-2 | sense | CTCTTTGTGATGGCCTTCCTG | [SEQ ID NO:51] | 464 |
| B7-2 | antisense | CTTAGGTTCTGGGTAACCGTG | [SEQ ID NO:52] | |
| G3PDH | sense | CCATGTTCGTCATGGGTGTGAACCA | [SEQ ID NO:53] | 251 |
| G3PDH | antisense | GCCAGTAGAGGCAGGGATGATGTTC | [SEQ ID NO:54] | | bp = base pairs.

Sense and antisense primers of each primer pair given by Table E1 were set at a different exon, respectively, to avoid DNA contamination. To assess the character of HMO6.A1 cells, the expression of cytokines (IL-1β, -2, -3, -4, -5, -6, -7, -8, -9, -10, -11, -12, -13, -15, and TNF-α), chemokines (macrophage inflammatory protein (MIP)-1α, MIP-1β, and monocyte chemoattractant protein (MCP)-1) was examined by RT-PCR. Total RNA was extracted using Trizol reagent (GIBCO-BRL, Gaithersburg, Md.). Complimentary DNA (cDNA) templates from each sample were prepared from 2 μg of total RNA primed with oligo dT primers (Pharmacia, Gaithersburg, Md.) using 400 units of MMLV reverse transcriptase (GIBCO-BRL) followed by 25 PCR amplification cycles (94° C. for 30 seconds, annealing at 60° C. for 60 seconds, and extension at 72° C. for 90 seconds). This cycle number allowed a linear cDNA dose-response. Glyceraldehyde-3-phosphate dehydrogenase (G3PDH) was used as a reaction standard [Ercolani et al., *J. Biol. Chem.* 263: 15335–15341 (1995)].

To confirm the purity of cell preparation, cDNA from microglia-enriched cultures were amplified for B7-2 (CD86, for microglia); GFAP (a cell type-specific marker for astrocytes); myelin basic protein (MBP, for oligodendrocytes); and neurofilament-M (NF-M, for neurons). For characterization of HMO6.A1 cells, mRNA expression of marker proteins specific for each cell type was also investigated. Gene expression of CD68, $P_{2Y1}$ purinergic receptor ($P_{2Y1}$R), $P_{2Y2}$R, CXCR4 which are expressed in embryonic human microglia (HM) was also examined in HMO6.A1 cells. Ten l of each PCR product was analyzed by 1.5% agarose gel electrophoresis. Authentic bands were determined by selective enzyme digestion.

Gene Expression of Cytokines and Chemokines Following Aβ Treatment

Gene expression of cytokines and chemokines in HM or HMO6.A1 cells was examined following a 6 hr treatment with or without 20 μM of Aβ$_{25-35}$ (NH$_2$-GSNKGAIIGLM-COOH). LPS at 100 ng/ml was used in microglial cultures since LPS is a potent activator of microglia [Gebicke-Haeter et al., *J. Neurosci.* 9: 187–194 (1989); Suzumura et al., *Brain Res.* 545: 301–306 (1991)].

ELISA Analysis

Production of TNF-α, IL-1β, IL-6, IL-8 or MIP-1α in normal human microglial cells or HMO6.A1 cells was determined in spent culture supernatants using ELISA kits specific for human TNF-α, IL-1β, IL-6, IL-8 or MIP-1α (R&D Systems, capable of detecting TNF-α at 4.4 pg/ml, IL-1β at 1 pg/ml, IL-6 at 0.70 pg/ml, IL-8 at 10 pg/ml and MIP-1α at 10 pg/ml). At the end of each experiment, culture supernatants were collected, centrifuged, and stored at –70° C.

Experimental Series I: Isolation of Human Microglia Cell Lines

Microglial-enriched populations were isolated from primary cultures of embryonic human telencephalon cells by virtue of differences in dish-adherent properties. The major differences are shown by FIGS. 2A–2D respectively.

Figure 2:
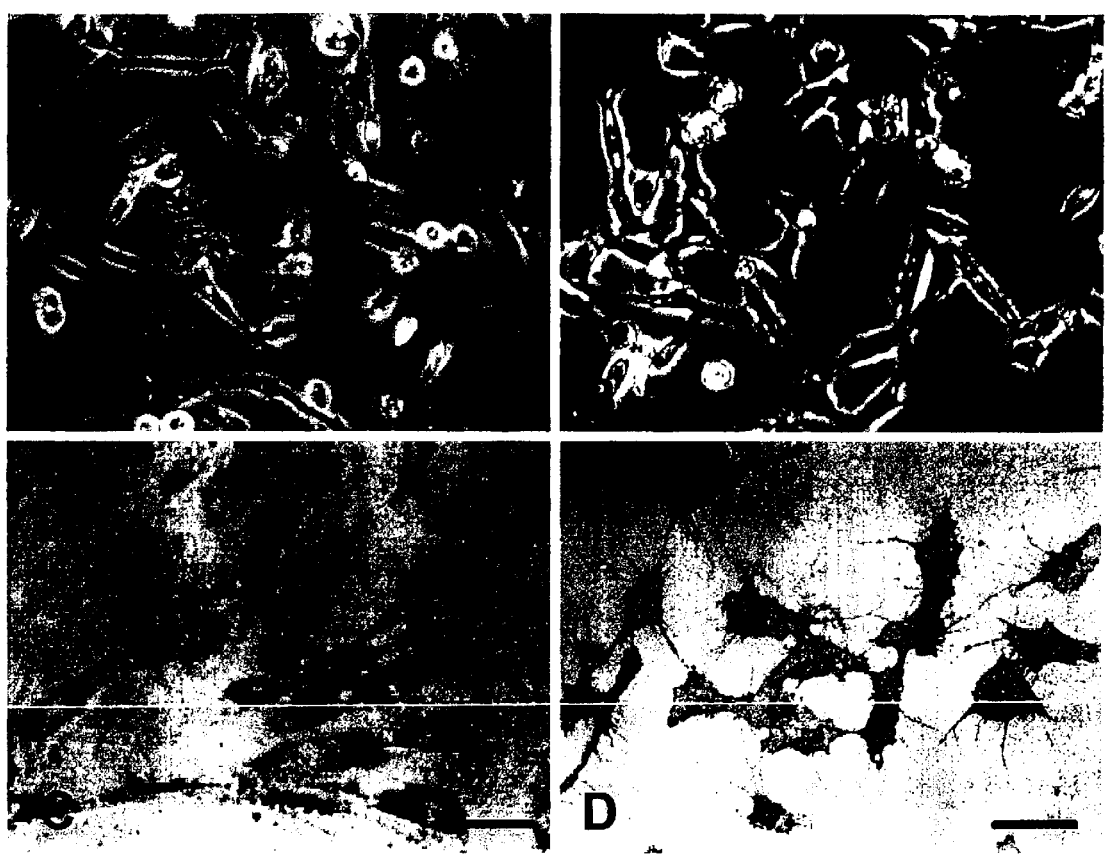
FIGS. 2A–2D are photographs illustrating the morphological appearance, antigenic attributes and functional capabilities of embryonic human microglia (HM) and the immortalized human microglia cell line HMO6.

FIG. 2 as a whole shows the morphological appearance, and antigenic and functional tests of HM and HMO6.A1 cells. FIG. 2A is a phase contrast microscopy of HM; and FIG. 2B of HMO6. FIG. 2C shows phagocytosis: latex beads are engulfed by HMO6; and FIG. 2D shows immunoreactivity in HMO6 for CD11b [Bar=20 μm].

As shown in FIG. 2B, human microglia are mostly round cells with filopodia surrounding the cell bodies or slender cells with several primary branches and were 8–12 μm in size. The purity of microglia cells in these cultures was more than 99%, as evaluated by RCA-1 or CD11b immunolabelling and confirmed by RT-PCR with positive message for B7-2 and negative messages for NF-M, GFAP, and MBP. These human microglia cells were infected with a retroviral vector encoding v-myc oncogene (PASK 1.2) to produce continuous microglia cell lines (see Methods).

One particular cell line proliferating after clonalization, HMO6 cells, had ramified morphology in the medium containing 5% fetal bovine serum and 5% horse serum (see FIG. 2B); but also changed their shape into ameboid form when these cells were plated at a low density. In the long-term culture (>15–20 passages), HMO6.Al cells phagocytose many debris in culture; tend to stretch their cell bodies; and grow slower. Accordingly, short-term cultures were used for investigation purposes.

Experimental Series II: Characterization of the HMO6 Human Microglia Cell Line

A series of experiments were then conducted based on the following empirical observations:

(i) HMO6.A1 cells adhered to glass or plastic substrate with a doubling time of 34.5 hr.

(ii) HMO6.A1 cells ingested latex beads actively during 2 hr incubation with beads (see FIG. 1C).

Experiment 1: Immunochemical Characterization

HMO6 cells cultured on glass coverslips (as shown by FIG. 2B) were found to be immunoreaction positive with antibodies specific for human mitochondria and pan-myc antigen, indicating that they are definitely human cells transfected with v-myc oncogene. The overall results are presented by Table E2 below.

TABLE E2

Utilized antibodies and results of immunohistochemical study

| Antigen | Specificity | Clone name | Subtype | Source | HM | HMO6.A1 |
|---|---|---|---|---|---|---|
| Human mitochondria | mitochondria | MAB1273 | IgG$_1$ | Chemicon | + | + |
| Pan-myc | myc | — | Polyclonal | Chemical | + | + |
| RCA-1 | microglia | — | Lectin | Sigma | ++ | ++ |
| CD11b | microglia | LM2/1.6.11 | IgG$_1$ | ATCC | ++ | + |
| CD68 | microglia | EMB11 | IgG$_1$ | Sigma | + | + |
| HLA-ABC | MHC class I | BB7.7 | IgG$_{2a}$ | ATCC | + | + |
| HLA-DR | MHC class II | L227 | IgG$_1$ | ATCC | + | + |
| MAP-2 | neuron | AP14 | IgG$_1$ | Sigma | − | − |
| β tubulin III | neuron | SDL.3D10 | IgG$_1$ | Sigma | − | − |
| GFAP | astrocytes | — | Polyclonal | DAKA | − | − |
| MBP | oligodendrocytes | — | Polyclonal | DAKO | − | − |

Antigen reactivity were determined by immunohistochemistry. Immunoreactivity was expressed in a scale ranging from − (negative) to ++ (strong positive).

As shown by FIG. 2 generally and Table E2, the HMO6.A1 cells were positively stained with RCA-1 (a plant lectin which recognizes surface antigen of microglia); and also expressed surface complement receptor 3 (CD11b), class II MHC antigen HLA-DR (a cell-type specific marker for activated microglia) and CD68 (a monocyte/macrophage marker).

Experiment 2: Ca$^{2+}$ Influx in HMO6.A1 Cells Following Exposure to ATP

The purinergic agonist ATP (at 100 μM) was applied to HMO6.A1 cells using calcium sensitive fluorescence microscopy. The results from a representative experiment are presented by FIGS. 3A and 3B which show an ATP-induced increase in [Ca$^{2+}$]i from n=7 cells.

FIG. 3 as a whole shows the increase of [Ca$^{2+}$]i induced by ATP. Application of ATP (at 100 μM) is indicated by the bar and response shown is from n=7 cells. Ionomycin was also applied (at 10 μM) following the ATP perfusion.

Figure 3A:
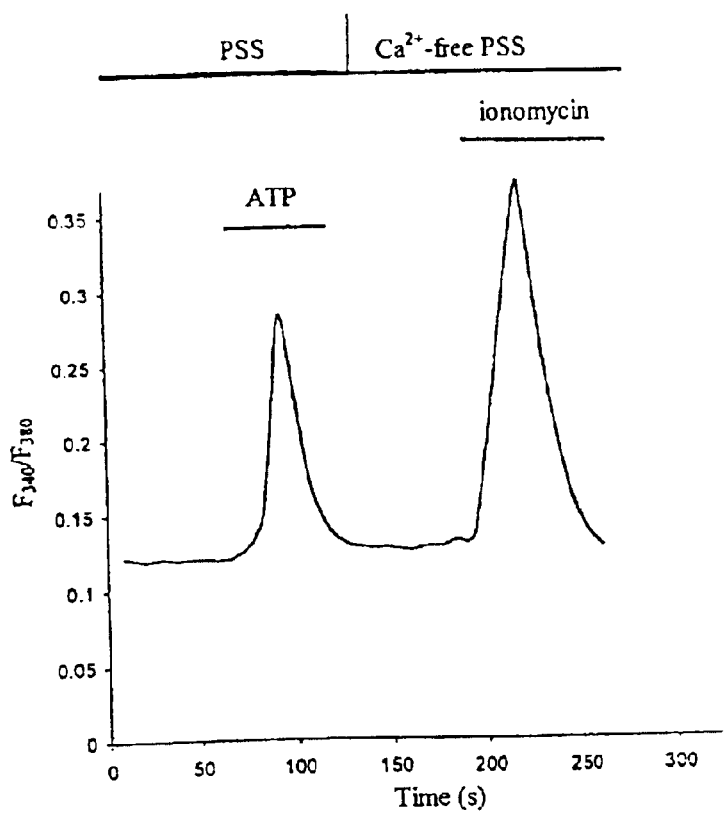
FIGS. 3A and 3B are graphs illustrating the increase of calcium ionophone ($Ca^{2+}$)i induced by ATP in HMO6 cells.
Figure 3B:
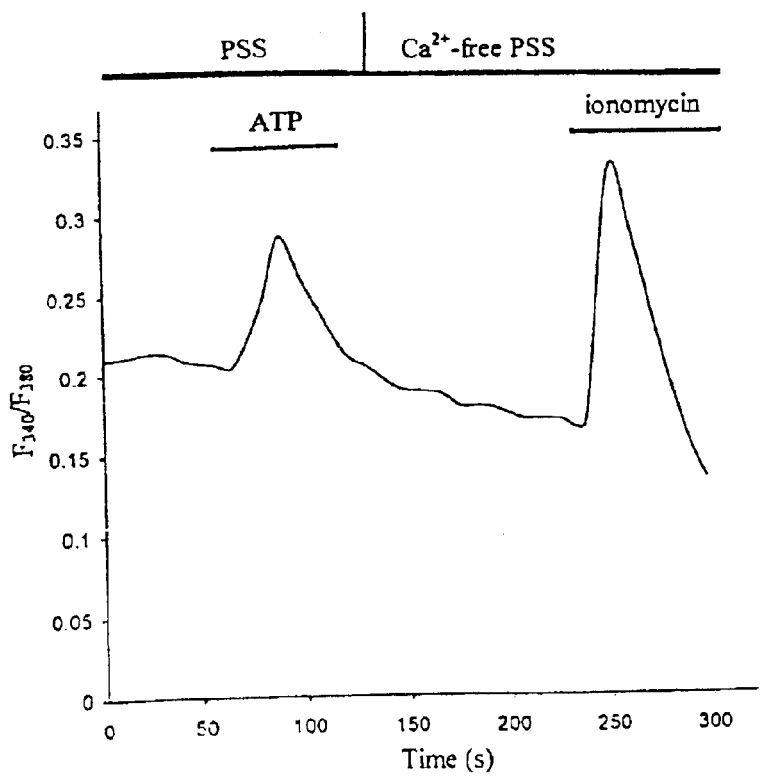

As shown by the graphs of FIGS. 3A and 3B, the response to ATP was rapid and transient with recovery from agonist application less than 30 s. Even in the maintained presence of ATP, the [Ca$^{2+}$]i declined to baseline levels. Similar responses were obtained with ATP applied in Ca$^{2+}$-free solutions (data not shown) indicating that the primary contributions to the increase in [Ca$^{2+}$]i was from internal stores. These empirical results are similar to those documented for ATP responses in cultured human microglia.

Figure 4A:
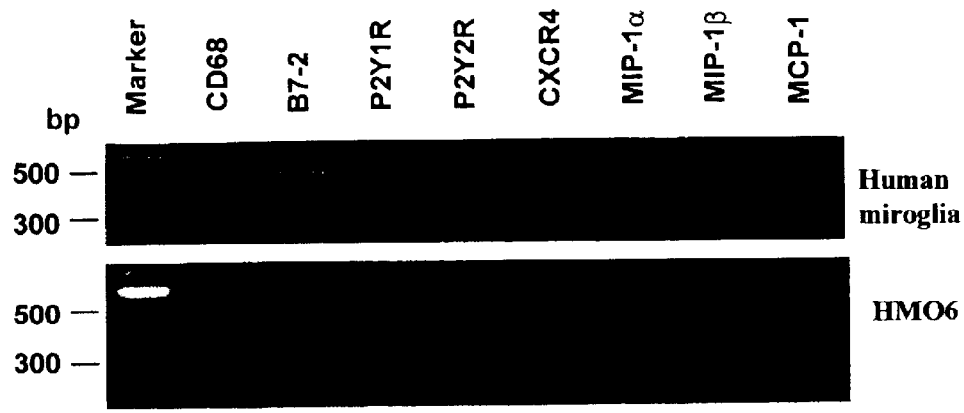
FIGS. 4A and 4B are photographs showing the detection of gene expression in HM and HMO6 cells.
Figure 4B:
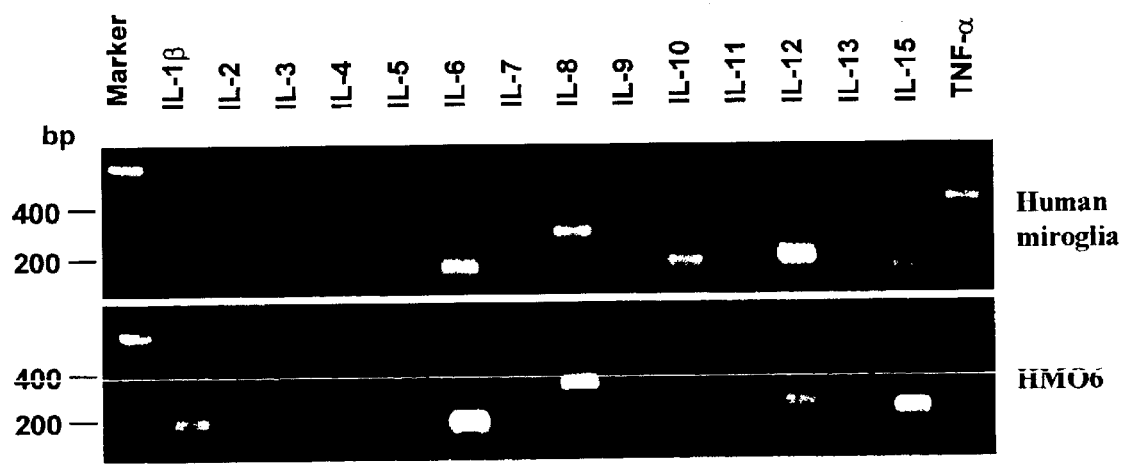

In addition, the effect of ionomycin on levels of [Ca$^{2+}$]i is shown by FIGS. 4A and 4B respectively. Specifically, FIG. 4 as a whole shows the detection of gene expression in HMO6.A1 and HM cells; and FIG. 4A shows the expression of specific genes for microglia and chemokine. Since B7-2, P$_{2Y2}$R and MIP-1α expressions were induced by TNF-α, gene expression in HMO6.A1 cells was shown following TNF-α treatment. Lane designation: M, 100 bp size marker; lane 1, CD68 (expected base pairs are 279); lane 2, B7-2 (464); lane 3, P$_{2Y1}$R (260); lane 4, P$_{2Y2}$R (367); lane 5, CXCR4 (206); lane 6, MIP-1α (393);lane 7, MIP-β (336); lane 8, MCP-1 (464). Expressions of specific gene for neuron (NF-M), for astrocytes (GFAP), and for oligodendrocytes (MBP) were not detected (data not shown).

In comparison, FIG. 4B shows the detection of cytokine gene expression in HMO6.A1 and HM cells. Since TNF-α gene expression was detected after 24 hr treatment with Aβ, gene expression in HMO6.A1 cells was shown following Aβ treatment. Lane designation: M, 100 bp size marker; lane 1, IL-1β (expected base pairs are 179); lane 2, IL-2 (301); lane 3, IL-3 (459); lane 4, IL-4 (337); lane 5, IL-5 (295); lane 6, IL-6 (159); lane 7, IL-7 (484); lane 8, IL-8 (301); lane 9, IL-9 (375); lane 10, IL-10 (194); lane 11, IL-11 (295); lane 12, IL-12 (213); lane 13, 1L-13 (198); lane 14, IL-15 (202); lane 15, TNF-α (490).

Overall, therefore, the Ca$^{2+}$ ionophore caused an increase in [Ca$^{2+}$]i which was considerably larger than the ATP-induced response. The response to ionomycin indicates the viability of HMO6.A1 cells.

Experiment 3: Characterization with RT-PCR

The results of RT-PCR analysis of HM and HMO6 cells are also shown by FIG. 4A. It is recognized that CD68 was expressed constitutively in unstimulated HMO6.A1 cells; and that B7-2, co-stimulatory antigen and a cell type-specific marker for microglia (32) was expressed after treating with TNF-α, but not with GM-CSF, IL-1β, IFN-γ, or LPS.

Since the existence of purinergic P$_{2Y}$ receptors is one of the characteristics in human microglia, the expression of P$_{2Y1}$ and P$_{2Y2}$ receptors in HMO6 cells by RT-PCR was also examined. Both P$_{2Y1}$ and P$_{2Y2}$ receptors were expressed in HM. However, in HMO6.A1 cells, P$_{2Y1}$ receptor was constitutively expressed; but P$_{2Y2}$ receptor was expressed only after treatment with GM-CSF, TNF-α, IL-1β, IFN-γ, or LPS. It was noted also that CXCR4 (a chemokine receptor that has drawn considerable attention as the co-receptors for HIV entry into human microglia) was expressed in both HM and HMO6.A1 cells.

Experiment 4: Cytokines and Chemokines Expression in HM and HMO6 Cells by RT-PCR The results of RT-PCR analysis of gene expression of cytokines and chemokines in HM and HMO6.A1 cells are also shown by FIG. 4 as a whole. In HM cells, MIP-1α, MIP-1β, MCP-1, IL-1β, -6, -8, -10, -12, -15 and TNF-a were detected in non-stimulatory state, while in HMO6.A1 cells, MIP-1β, MCP-1, IL-1β, -6, -8, -12, and -15 were expressed in non-stimulating state. TNF-α was expressed in HM, but was recognized in HMO6.A1 cells only after treatment with TNF-α for 4 hr and not with IL-1β or IFN-γ. Also, MIP-1α expression was detected after 24 hr treatment with TNF-α in HMO6.A1 cells; and IL-10 expression was detected in HM cells, but not in HMO6.A1 cells.

Experimental Series III: Effect of β-amyloid in HM and HMO6 Cells

Subsequently, gene expression of cytokines and chemokines in HM and HMO6.A1 cells was examined. As the number of cells, and therefore RNA, was limited, analysis of gene expression was carried out using RT-PCR method. The results are shown by FIG. 5 and FIGS. 6A–6E respectively.

Figure 5:
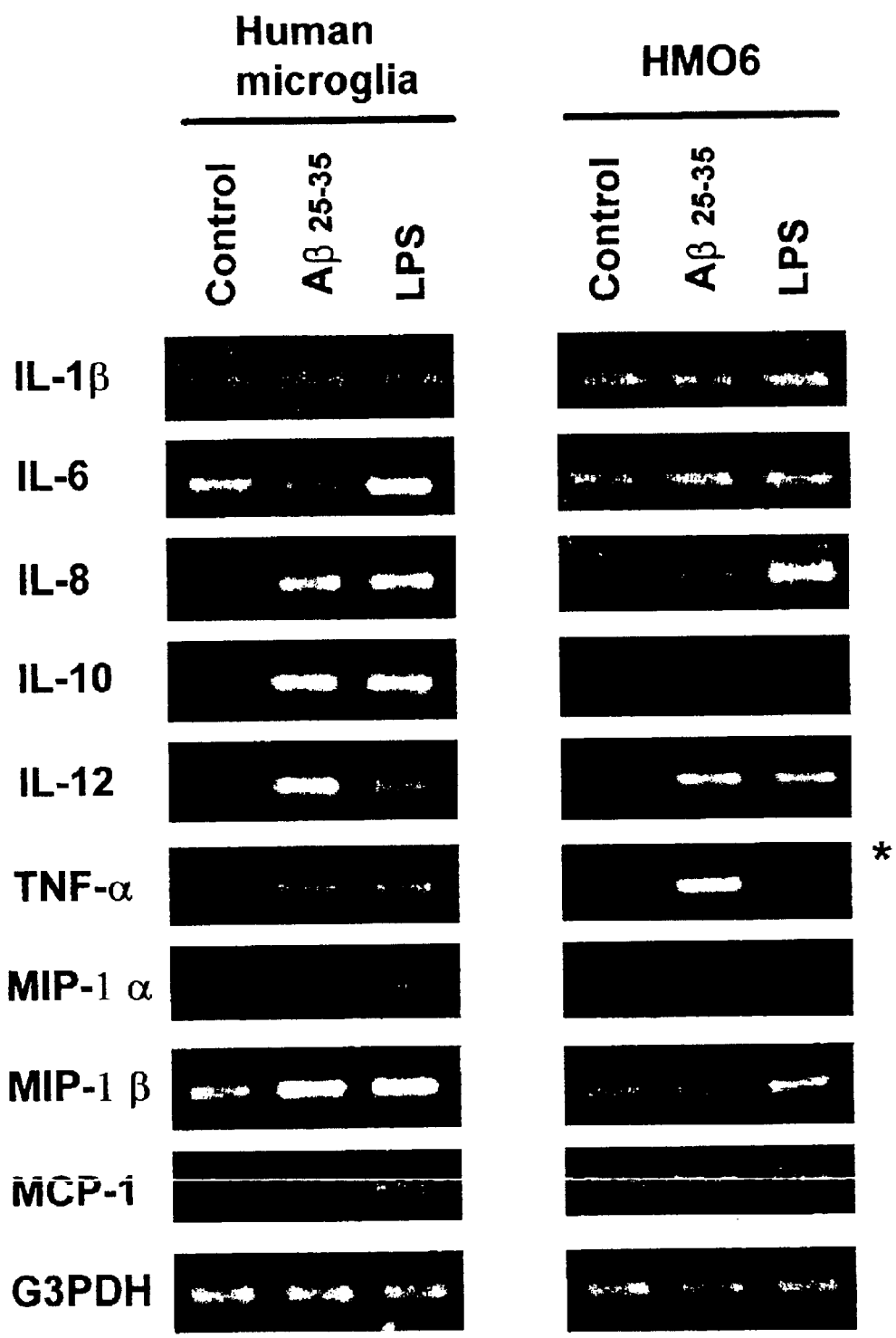
FIG. 5 is a photograph illustrating the effect of $A\beta_{25-35}$ and LPS on cytokine and chemokine expression and the effect of $A\beta_{25-35}$ on CXCR4 in RNA expression in HM and HMO6 cells.
Figure 6A:
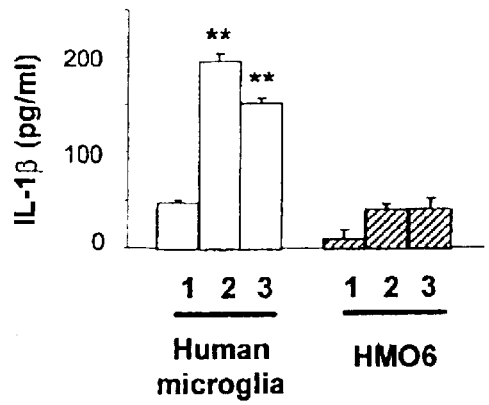
FIGS. 6A–6B are graphs showing the results of ELISA analyses for cytokines and chemokines released from normal human microglia and HMO6 immortalized human microglia cells.
Figure 6B:
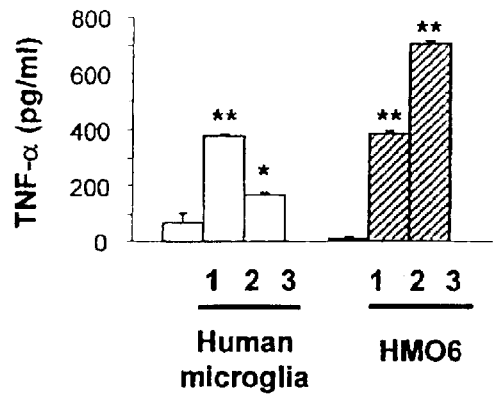
Figure 6C:
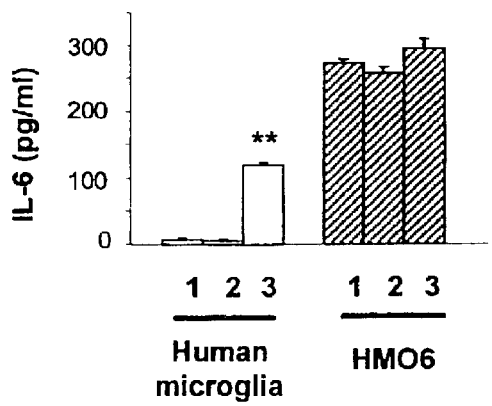
Figure 6D:
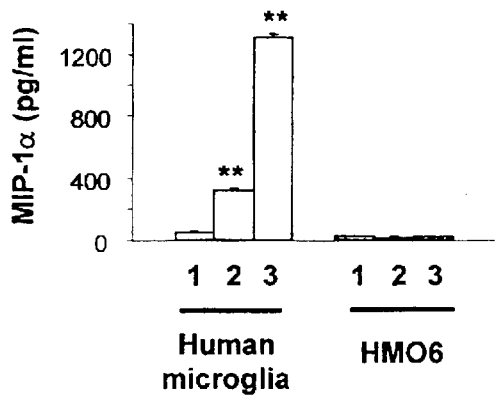
Figure 6E:
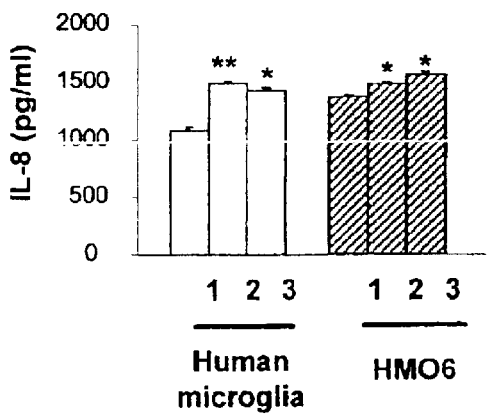

As seen in FIG. 5, the effect of $A\beta_{25-35}$ and LPS on cytokines, chemokines, and CXCR4 mRNA expression in HM and HMO6.A1 after treating with $A\beta_{25-35}$ for 6 hrs by RT-PCR is revealed. Glyceraldehyde-3-phosphate dehydrogenase (G3PDH) was used as a reaction standard. After gel electrophoresis in 1.4% agarose, the reaction products were stained with ethidium bromide and photographed.

Since expression signals were generally recognized strongly at 3–6 hr treatment, the gene expression levels at 6 hr following $A\beta_{25-35}$ treatment were examined. Among inflammatory cytokines, TNF-α expression was markedly elevated and IL-1β expression slightly increased in HM with $A\beta_{25-35}$ treatment. In HMO6.A1 cells, TNF-α expression was not induced by $A\beta_{25-35}$ and LPS after 6 hr incubation, but was induced after 24 hr (see FIG. 3). However, no change in IL-1β and IL-6 expression was found. Expression of IL-12, an NK cell stimulatory factor was elevated in both HM and HMO6.A1 cells following $A\beta_{25-35}$ treatment.

Also, among anti-inflammatory cytokines, IL-4 and IL-13 expressions were not recognized after $A\beta_{25-35}$ treatment, but IL-10 expression was increased with $A\beta_{25-35}$ in HM. In HMO6.A1 cells, IL-10 expression was not detected after $A\beta_{25-35}$ treatment. In HM, mRNAs for chemokines, including IL-8, MIP-1α, MIP-1β and MCP were up-regulated after Aβ treatment, while in HMO6.A1 cells, elevated expression of IL-8 and MCP was detected, but MIP-1α was not expressed. No change in MIP-1β expression was found. CXCR4 expression was increased with $A\beta_{25-35}$ and LPS treatment in HMO6.A1 cells, but not in HM.

The production of cytokines and chemokines following $A\beta_{25-35}$ treatment in cultures of HM and HMO6.A1 cells by ELISA method was also examined. The results are presented by FIGS. 6A–6E respectively.

FIGS. 6A–6E are graphs presenting ELISA analyses of cytokines and chemokines released from normal human microglia and HMO6 immortalized human microglia cell line. Cells were plated in 6-well plates, stimulated for 48 hours with or without 20 ug/ml β-amyloid or 10 ng/ml LPS, and then cytokine/chemokine production in spent media was measured. Values represent mean±SEM from 3 experiments.

As shown by FIG. 5, among the pro-inflammatory cytokines, TNF-α showed a marked increase in both HFM and HMO6.A1 cells. Also, it will be noted that the release of IL-1β into culture medium was demonstrated in HM after treatment with $A\beta_{25-35}$; and LPS. IL-6 levels in the culture supernatant were not increased in $A\beta_{25-35}$ treated cultures, but increased after LPS treatment. In chemokines, the levels of IL-8 in the supernatant of HM and HMO6.Al cells treated with $A\beta_{25-35}$ and LPS were greater than the levels in non-treated controls. MIP-1α levels in HM were elevated after incubation with $A\beta_{25-35}$. As no expression of MIP-1α was detected in HMO6.A1 cells, the amount of release from HMO6.A1 cell cultures was very low in spite of stimulation.

Figure 7:
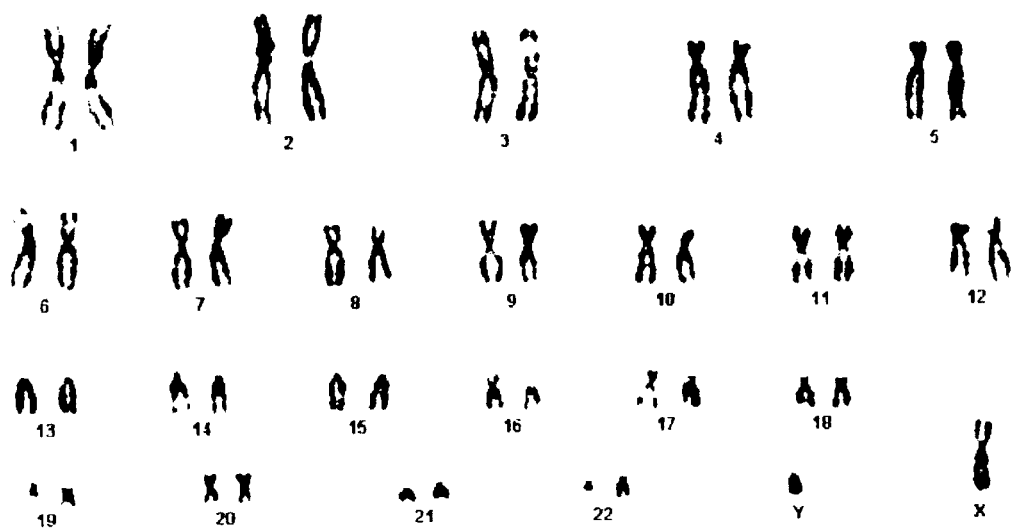
FIG. 7 is a photograph shows the cytogenetic analysis of HMO6 immortalized human microglia cells as the normal karyotype of human cells.

Lastly, FIG. 7 shows the cytogenetic analysis of HMO6 immortalized human microglia cells line; and indicates that the microglia cells possess normal karyotype of human cells with a 46 XY karyotype without ayn chromosomal abnormality.

Conclusions Based Upon Empirical Results

1. The immortalized human microglial cell line, HMO6 expresses not only the markers CD68 and RCA-1 lectin, but also HLA-ABC (MHC class I antigen), HLA-DR (MHC class II antigen), and CD11b, which are cell type specific markers for microglia and cells of monocyte/macrophage lineage. Moreover, mRNA for B7-2, a co-stimulatory molecule, was induced after 24 hr incubation with TNF-α, suggesting that HMO6 cells can function as antigen presenting cells. Since inflammatory and immunological responses can be mediated by these surface antigens, HMO6.A1 cells can serve as a model system for immune surveillance in CNS. Also, since B-7 is expressed in human microglia, but not in human astrocytes, it is demonstrated that HMO6 cells are derived from human microglia and not from other CNS cell types (including astrocytes).

2. The expression of purinergic receptors was found in HMO6 cells since ATP caused a transient increase in levels of $[Ca^{2+}]i$. These responses were similar to ones obtained with application of ATP to human fetal microglia. However, in human fetal microglia, the major contribution to ATP responses was depletion of endoplasmic stores, with this process coupled to agonist activation of the $P_{2Y}$ type of receptor. In comparison, the increase in $[Ca^{2+}]i$ induced by ATP in immortalized microglia was smaller relative to the effects of the $Ca^{2+}$. This observed difference reflects a small contribution of $Ca^{2+}$ influx through store-operated channels compared with ionomycin.

3. HMO6 cells had almost consistent expression pattern with embryonic human microglia (HM). However, TNF-α gene expression in immortalized microglia was induced after 4 hr incubation with TNF-α or after 24 hr contact with Aβ or LPS. It is noted that a previous study demonstrated that microglial progenitor cells present in the newborn mice forebrain did not express any of the microglia/macrophage-related antigenic markers; and in the presence of appropriate trophic factors, such progenitor cells gave rise to microglia. As empirically shown herein, TNF-α induced the gene expression of TNF-α after 4 hr reactive time and also induced B7-2 and MIP-1α after 24 hr HMO6 cells derived from human fetal microglia thus are deemed to be in a state similar to microglia progenitor cells.

4. Among pro-inflammatory cytokines, the empirical data shows that TNF-α mRNA expression and protein production are increased in both HM and HMO6 cells. Also, although IL-1β mRNA expression was not raised for 6 hr, the released IL-1β in HM cultures incubated after 48 hr was increased. This was consistent with the results that IL-1β, mRNA expression increases over the 48-hrs study period after amyloid addition. These results indicate that the immortalized human microglia cell line reproduces most of molecular and immunological features of normal human microglia closely.

5. Expression of cytokines/chemokines IL-6, IL-8, IL-10, IL-12, TNF-α, MIP-1α, MIP-1 and MCP-1 was elevated in normal human microglia cells following treatment with microglial activators such as LPS or β-amyloid, while in HMO6 immortalized microglia cells expression of IL-8, IL-12, MIP-1α and MCP-1 was elevated. These results indicate that HM06 immortalized human microglia cells are deemed to be phenotypically similar to normal human microglia cells. In addition expression of TNF-α and MIP-1α was newly induced in HMO6 immortalized microglia cells following treatment with TNF-α.

The present invention is not to be limited in scope nor restricted in form except by the claims appended hereto.

What I claim is:

1. A genetically modified human microglia cell which can be maintained as a stable, substantially homogeneous cell line in-vitro, said genetically modified cell comprising:
   a microglia cell of human origin which is stable when maintained in culture and which
   (i) has demonstrable phagocytic properties;
   (ii) produces substantially homogenous progeny continuously while maintained in culture;
   (iii) presents at least CD11b and CD68 as surface antigens; and
   (iv) contains human genomic DNA which has been genetically modified to include a viral vector carrying at least one DNA segment encoding an exogenous gene for intracellular expression wherein said viral vector is an amphotrophic retroviral viral vector and wherein said viral vector includes an exogenous DNA sequence encoding a v-myc gene.

2. The genetically modified human microglia cell as recited in claim 1 further comprising the presence of the surface antigen RcA-lectin.

3. The genetically modified human microglia cell as recited in claim 1 further comprising the presence of $P_{2Y1}$ receptors.

4. The genetically modified human microglia cell as recited in claim 1 further comprising the presence of the surface antigens HLA-ABC (MHC class I) and HLA-DR (MHC class II).

5. The genetically modified human microglia cell as recited in claim 1 wherein said cell expresses at least one active substance selected from the group consisting of cytokines and chemokines.

6. The genetically modified human microglia cell as recited in claim 5 wherein said expressed active substance is selected from the group consisting of M1P-1β, MCP-1, IL-1β, IL-6, IL-8, IL-12, and IL-15.

7. The genetically modified human microglia cell as recited in claim 1 wherein said cell is in a non-stimulated state.

8. The genetically modified human microglia cell as recited in claim 1 wherin said cell is in a stimulated state.

9. The genetically modified human microglia cell as recited in claim 8 wherein said stimulated cell overexpresses at least one pharmacologically active substance selected from the group consisting of cytokines and chemokines.

10. A method for transforming human microglial cells into a genetically modified microglial cell line of claim 1, said method comprising:
    (a) obtaining human microglial cells;
    (b) culturing said human microglial cells;
    (c) transfecting said cultured human microglial cells using an amphotrophic replication incompetent retroviral vector encoding a v-myc oncogene; and
    (d) expanding said transfectants in culture media as an immortalized, substantially homogeneous cell line.

* * * * *